United States Patent [19]

Reddy

[11] Patent Number: 5,325,871
[45] Date of Patent: Jul. 5, 1994

[54] FEMALE CONDOM

[76] Inventor: Alla V. K. Reddy, 9 Webster Ct., Plainsboro, N.J. 08535

[21] Appl. No.: 702,185

[22] Filed: May 20, 1991

[51] Int. Cl.⁵ .............................................. A61F 6/06
[52] U.S. Cl. .................................... 128/830; 128/844
[58] Field of Search ............... 128/830, 832, 834, 837, 128/841, 842, 844, 918

[56] References Cited

U.S. PATENT DOCUMENTS

| 3,128,762 | 4/1964 | Young | 128/844 X |
| 3,536,066 | 10/1970 | Ludwig | 128/842 X |
| 4,446,860 | 5/1984 | Gutnick | 128/844 |
| 4,875,490 | 10/1989 | Quiroz | 128/842 X |
| 4,972,849 | 11/1990 | Park et al. | 128/844 X |
| 4,976,273 | 12/1990 | Hessel | 128/844 |

FOREIGN PATENT DOCUMENTS

| 3723458 | 1/1989 | Fed. Rep. of Germany | 128/830 |
| 2530140 | 1/1984 | France | 128/830 |
| 2153686 | 8/1985 | United Kingdom | 128/830 |
| 9000038 | 1/1990 | World Int. Prop. O. | 128/918 |

Primary Examiner—Robert A. Hafer
Assistant Examiner—Sam Rimell
Attorney, Agent, or Firm—Reising, Ethington Barnard, Perry & Milton

[57] ABSTRACT

A female condom has a pouch with an unlubricated surface without spermicides to prevent vaginal infection and a lubricating and retention member is provided having voids therein filled with a lubricant and spermicides to lubricate the interior of the pouch when the sponge member is inserted into the pouch; the retention member includes a tip for piloting the retention member into the interior of the pouch and the retention member further includes a recessed head portion that is compressible to permit insertion of the retention member into the pouch and that is expandable to force the outer surface of the pouch against the surface of the vagina for holding the pouch against withdrawal during coitus; the recess in the head portion is located in axial alignment with an erected penis to accommodate the penis during use.

1 Claim, 1 Drawing Sheet

FEMALE CONDOM

FIELD OF THE INVENTION

This invention relates to prophylactic devices and more particularly to female condoms having a pouch portion insertable into the vagina.

BACKGROUND OF THE INVENTION

With the widespread prevalence of venereal disease and the growing occurrence of AIDS (acquired immune deficiency syndrome), there is an increasing need for effective means to prevent the transmission of such diseases through sexual contact and resultant exchange of bodily fluids between a user and the user's partner.

Heretofore, conventional means for preventing the transmission of such bodily fluids and exposure to such diseases because of bodily contact have included the use of condoms, diaphragms, jells, creams and the like.

Additionally, there have been proposals to provide female prophylactic devices which can be worn by a female prior to use and disposed of following use. While such conventional and proposed devices are suitable for their intended purpose, it has been found that they are not totally effective for various reasons.

One example of a prior prophylactic device for use by females is that set forth in U.S. Pat. No. 3,536,066. The '066 patent shows a pant styled garment having a bellow configured pouch thereon which is located on the exterior of the pant. The bellows is preinsertable into the vaginal canal of a female prior to use. After the bellows is inserted, convolutions therein are extended to provide for extension of the bellows to accommodate an erected penis during use of the contraceptive device. The device requires preinsertion of a segment of the bellows and does not include means for piloting a large pouch-like member into a vaginal canal. Furthermore, the garment portions of the device are formed from rubber material which is configured to contact a large portion of the waist region of the user as well as the buttocks and hip regions of a user so as to cause possible irritation and discomfort when worn for substantial periods of time prior to use.

U.S. Pat. Des. No. 254,808 to Meldahl discloses a device for use as a male contraceptive. While the contraceptive has a larger diameter than typical condoms, it does not include a portion thereon which will serve as the device to prevent the passage of bodily fluids between a user and a partner. There are not straps to hold the device in place.

German Patentscrifft No. 210,143 (1909) discloses a female contraceptive device having a pouch that includes a generally circular collar on the other end thereof. There is no suggestion to provide a portion of the device that will cover and conform to the full perineum region of a user. Furthermore, there is no suggestion of how to hold the device in place during use. Furthermore, the outer lip or collar of the condom can enter the vagina during intercourse so as to cause undesirable exposure of the users to the other's bodily fluids.

U.S. Pat. No. 4,735,621 likewise shows a thin walled, condom-like, tubular protective device for insertion into a vaginal canal. It includes a resilient ring on one end thereof to anchor the device in the vaginal canal.

The retention ring of the '621 patent is an integral part of the condom which requires special manufacturing tooling. Furthermore, the retention ring is configured to have a diameter corresponding to that of the pouch and a cross-sectional diameter that is small compared to the diameter of the ring. As a consequence the ring requires careful placement within the vagina so as to assure that it will fit in an interference relationship therewith to prevent the pouch from being withdrawn during coitus. Furthermore, the '621 retention ring may be oriented in a direction that will produce undesirable contact with an erected penis. Furthermore, the outer ring goes into the vagina during intercourse causing undesirable exposure of the users to bodily fluids.

Furthermore, JAMA, Jan. 2, 1991, Vol. 265, No. 1, page 54 includes an article entitled, "Escherichia coli Bacteriuria and Contraceptive Method", by Hooton, M. D., et al. The article reports that the use of spermicidal lubricants on the outer surface of condoms can increase vaginal infections.

The aforesaid devices are either uncomfortable garment type devices or are devices which can slip from a desired seated relationship during use to cause undesirable exposure of the user to the exchange of bodily fluids between the user and the user's partner.

SUMMARY OF THE PRESENT INVENTION

In the present invention the problem of inadvertent withdrawal of the pouch and or misplacement of a retention ring are avoided by the provision of a prophylactic device having a separately insertable retention member that is compressible during insertion into the interior of a pouch portion of a female condom and which expands against the inner surface of the pouch portion adjacent the closed end of the pouch to press the outer surface of the pouch against the vagina for holding the pouch in place during coitus.

One feature of the present invention is to provide a retention member which is a lubricating and retention member which includes voids within the retention member to receive material for lubricating the interior of the pouch with a spermicidal lubricant as the retention member is inserted therein. Coverage of the outer surface of pouch with spermicidal lubricant is prevented. Accordingly, selective lubrication is obtained without increasing the risk of vaginal infection.

Another feature of the present invention is to form the retention member of a sponge-like material having the voids formed integrally thereof for filling with lubricants and spermicides to lubricate the interior of the pouch.

Still another feature of the present invention is to form a retention member with a head portion having a diameter greater than the tip portion and wherein the head portion is compressible to a reduced dimension during insertion of the retention member and which is expandable to a diameter that will direct a retention force against the pouch and the vagina for retaining the pouch in place during coitus.

Yet another feature of the present invention is to form the retention member as a unitary member of sponge-like compressible material having voids for holding a lubricating and spermicidal material for lubricating only the interior of the pouch as the retention member is inserted into the pouch adjacent a closed end thereof; the unitary member having a piloting tip and further including a compressible head portion that assumes a reduced dimension during insertion and which will expand to hold the pouch in place during coitus; and wherein the compressible head portion includes a recess in the end thereof located in axial alignment with an erected penis for accommodating the penis during coitus.

BRIEF DESCRIPTION OF THE DRAWINGS

Other advantages, features and objects of the present invention will become more apparent from the following detailed description when taken in conjunction with the appended drawings wherein.

DETAILED DESCRIPTION OF A PREFERRED EMBODIMENT OF THE INVENTION

Figure 1:
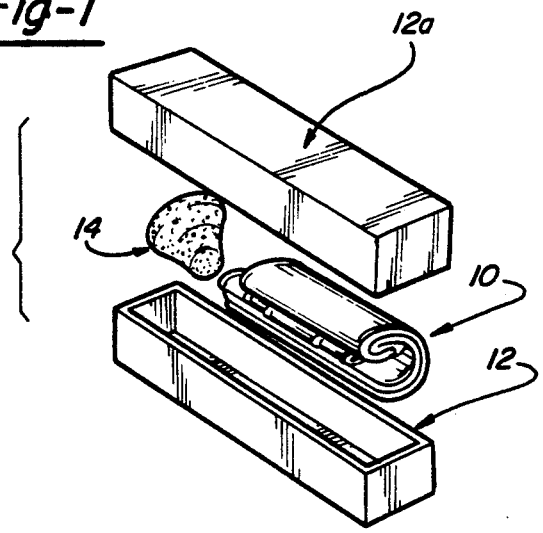
FIG. 1 is a perspective view of the component parts of the invention prior to use.

Referring now to FIG. 1, a female condom 10 is shown rolled up for packing in a box 12 with a cover 12a. A retention member 14 of the present invention is also shown in one suitable packing configuration prior to its insertion into the female condom 10.

When ready for use the female condom 10 is unrolled to form a pouch 16 and a shield portion 18. More particularly, the pouch 16 has a tubular portion 19 and closed end 20 that is insertable into the vagina and the pouch 16 has an open end 22 that is connected to the shield portion 18. The shield portion 18 is shaped like the shield portion of the female condoms shown in my issued U.S. Pat. Nos. 4,993,431 and 4,993,433 which are incorporated by reference as showing pouches with closed ends that are suitable for use with the retention member 14 of the present invention.

The prophylactic device can have various sizes and wall thicknesses in accordance with the invention. For example, the pouch 14 may have a length in the range of 1 to 10 inches, preferably about 4 to 6 inches and its maximum diameter will vary from 1½ to 4 inches. While the pouch 14 is shown as having a uniform circular cross-section throughout its length, the cross-section of the shape can vary along the length. The thickness of the wall material of the prophylactic device may also vary. For example, it can be as thin as 0.0005 inches or as thick as 0.1 inches. Preferably the wall thickness will be in the range of about 0.001 to 0.005 inches. While the material for forming the deposited material is preferably made of elastic impermeable substances such as natural rubber (e.g., latex), synthetic rubber (e.g., silicon rubber), or polyurethane. Other useful materials include nonelastic material such as various plastics including polyethylene.

In the specific illustration of FIGS. 1 through 4, the prophylactic device 10 is made of latex material. The wall thickness of the unreinforced portions of the prophylactic device 10 is 0.0035 inches and the wall thickness of the reinforcing portions can be slightly thicker.

The overall unstretched width of the shield portion 18 of the prophylactic device 10 is 6.5 inches and the overall length of the shield portion 18 is 8 inches. Leg openings have an unstretched width of 0.875 inches and a length of 7¼ inches.

The length of the pouch is in the order of 6 inches and its diameter is approximately 2 inches.

The aforesaid dimensions are cited for illustrative purposes only, with it being understood that dimensions are selected so that the prophylactic device 10 can be configured to anatomically relate to the perineum region of either a female user of the prophylactic device 10 or a male user of the device. In either case, once the prophylactic device 10 is located over the perineum of the user, the pouch 14 can be rolled from its stored position in close spaced relationship with the plane of the shield 18 to an extended position within a body cavity of a user.

Figure 2:
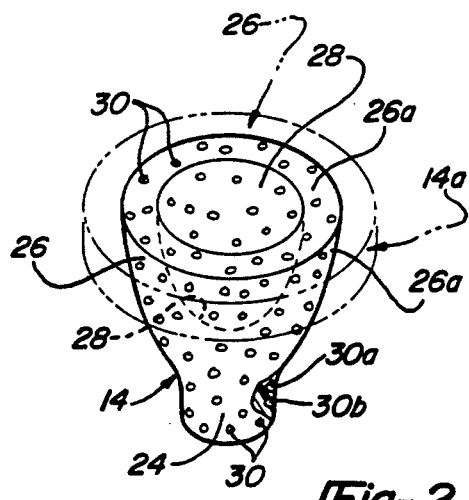
FIG. 2 is a perspective view of a retention device shown compressed for insertion.
Figure 3:
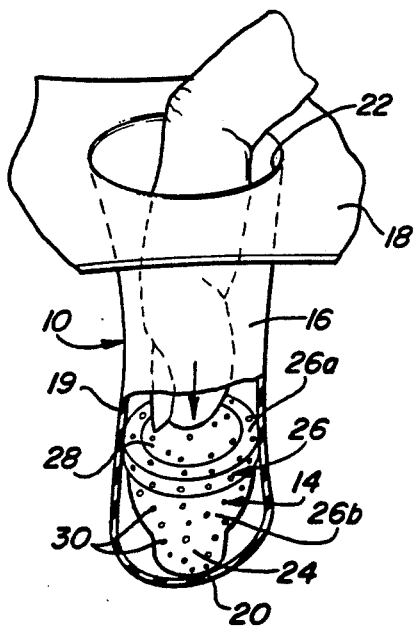
FIG. 3 is a perspective view, partially sectioned, of the invention following insertion and expansion of the retention member into biasing engagement with the pouch portion of a female condom.

In one aspect of the present invention, the retention member 14 is shown compressed in FIG. 2 in preparation for insertion into the pouch 16. The expanded position of the retention member is shown by broken lines 14a. As shown, the retention member 14 is a unitary member having a tip portion 24 that is bullet shaped to define a pilot portion on the retention member 14 that will guide the retention member 14 as it is being inserted into the pouch 16 as shown in FIG. 3. It is understood that the pouch 16 is unrolled into the vagina as the retention member 14 is inserted therein. In another aspect of the invention, the unitary retention member 14 includes an enlarged head portion 26 that is compressible into a reduced dimension during insertion of the unitary retention member 14 into the pouch 16. The enlarged head portion 26 has its greatest dimension at a rim 26a adjacent a recessed surface 28 in the end of the retention member. The enlarged head portion 26 further includes a generally conical surface 26b that extends between the rim 26a and the tip portion 24 to provide a gradual interlock of the pouch 16 between the retention member 14 and the wall of the vagina when the retention member 14 is in place as shown in FIG. 3. The retention member 14 is located adjacent the closed end 20 when in its retaining position. In this position, the compressed head portion 26 is fully expanded so that it will bias the wall of the pouch 16 against the vagina so as to firmly hold the closed end 20 of the pouch 16 within the vagina during coitus.

Yet another aspect of the present invention is that the enlarged head portion 26 includes the recessed surface 28 in a location when assembled within the pouch 16 that is aligned with an erect penis. The recessed surface 28 has a depth which will accommodate the glans penis of the erect penis so as to avoid undesirable contact between the penis and the retention member 14.

Still another feature of the present invention is that the retention member is formed of a porous material such as natural sponge material or a suitable soft porous sponge-like natural or synthetic material having voids 30 therein corresponding to those found in natural sponge material. Suitable materials include natural sponge materials; soft rubber open lattice material; polyurethane foams of the open cell blown foam type and the like. The voids 30 are shown in the enlarged fragmentary sectional view of FIG. 2 as having a cavity portion 30a and an open end 30b facing the exterior surfaces of the tip portion 24, the head portion 26 including the rim 26a and the conical surface 26b. The voids 30 are filled with a suitable material such as lubricating or spermicidal gels such that the inner surfaces 16a of the pouch 16 will be coated with a layer of lubricating material during insertion of the retention member 14 into the interior of the pouch. The voids 30 also are formed on the recessed surface 28 to provide a lubricated surface between the penis and the inserted and interlocked retention member 14.

While the retention member 14 is described herein as combining both lubrication and retention functions, the invention encompasses retention devices without the lubricant features.

Figure 1A:
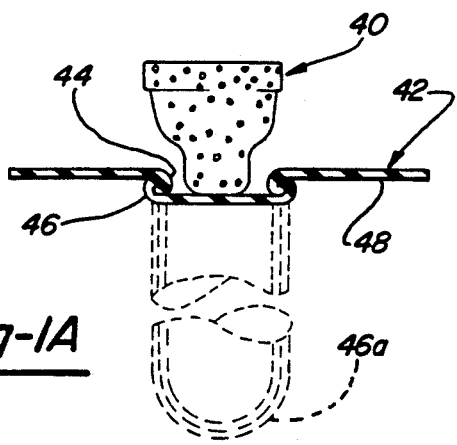
FIG. 1A is a fragmentary view of a preassembled embodiment of the invention.

Yet another embodiment of the invention is shown in FIG. 1A wherein a lubricating and retention member 40 is preassembled within a female condom 42 so that they can be packaged as a unit. The female condom includes an entrance 44 in which the lubricating and retention member 40 is preassembled so as to be ready for use when the female condom 42 is unpackaged. A pouch 46 is rolled against a shield 48 so that it will receive the lubricating and retention member 40 as it is inserted therein.

Figure 4:
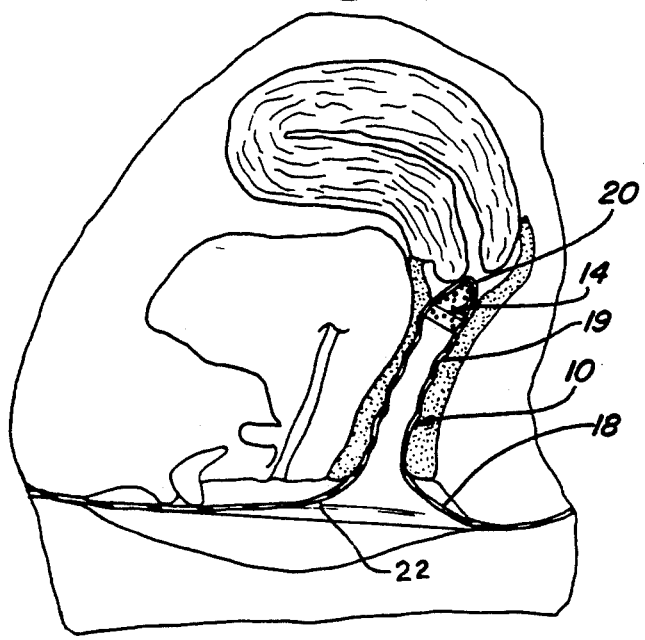
FIG. 4 is a sectional view of the invention shown in place.

The rolled pouch 46 extends to a double wall telescoped pouch 46a as the member 40 is inserted. The pouch 46a fully unrolls on further insertion of the member 40 until the pouch 46 is fully disposed and retained in the vagina as shown in FIG. 4.

While the best mode for carrying out the invention has herein been described in detail, those familiar with the art to which this invention relates will recognize various alternative designs and embodiments for practicing the invention as defined by the following claims.

What is claimed is:

1. In a female condom having a pouch with a closed end and a tubular portion insertable into a vagina and the pouch further including an open end thereon connected to a shield portion secured to the pouch for covering the perineum of a user the improvement comprising:

a retention member insertable within the pouch following insertion of the pouch within a vagina; said retention member including a head portion having a continuous circumferentially formed rim and a conical outer surface and a tip portion having a bullet-like shape with an outer surface thereon integrally joined to said conical outer surface; said head portion rim having an outer diameter greater than the greatest diameter of said conical outer surface and said rim being compressible for insertion of said retention member tip first into said pouch; said head portion rim being expandable with respect to the pouch adjacent the closed end of said pouch following insertion therein for forcing the pouch against the vagina so as to secure the pouch within the vagina against separation from the vagina during coitus and said retention member having an interiorly located conically shaped surface extending to said rim and surrounded at one end thereof by said rim; said conically shaped inner surface having a depth for covering the glans penis of a penis and combining with said rim to form a smooth uninterrupted surface for receiving the glans penis therein during coitus.

* * * * *